United States Patent [19]

Nadolink

[11] Patent Number: 5,728,944
[45] Date of Patent: Mar. 17, 1998

[54] PHOTOELASTIC STRESS SENSOR

[75] Inventor: Richard H. Nadolink, Portsmouth, R.I.

[73] Assignee: The United States of America as represented by the Secretary of the Navy, Washington, D.C.

[21] Appl. No.: 605,291

[22] Filed: Jan. 17, 1996

[51] Int. Cl.⁶ ............................................. G01L 1/24
[52] U.S. Cl. ............................................. 73/800; 73/760
[58] Field of Search ....................... 73/800, 801, 760, 73/860

[56] References Cited

U.S. PATENT DOCUMENTS

| | | | |
|---|---|---|---|
| 4,353,649 | 10/1982 | Kishii | 73/800 |
| 4,789,236 | 12/1988 | Hodor et al. | 73/800 |
| 4,939,368 | 7/1990 | Brown | 73/800 |
| 5,426,498 | 6/1995 | Brueck et al. | 73/800 |
| 5,438,879 | 8/1995 | Reda | 73/800 |
| 5,546,811 | 8/1996 | Rogers et al. | 73/800 |

*Primary Examiner*—George M. Dombroske
*Assistant Examiner*—Max H. Noori
*Attorney, Agent, or Firm*—Michael J. McGowan; Michael L. Oglo; Prithvi C. Lall

[57] ABSTRACT

A stress detection apparatus is provided. A piece of semiconductor grade, single crystal silicon mounted on the material is illuminated by an infrared source with radiation having a wavelength in the range of 800–1100 nanometers. An infrared detector monitors the photoelastic effects of illuminating the single crystal silicon with the radiation.

17 Claims, 1 Drawing Sheet

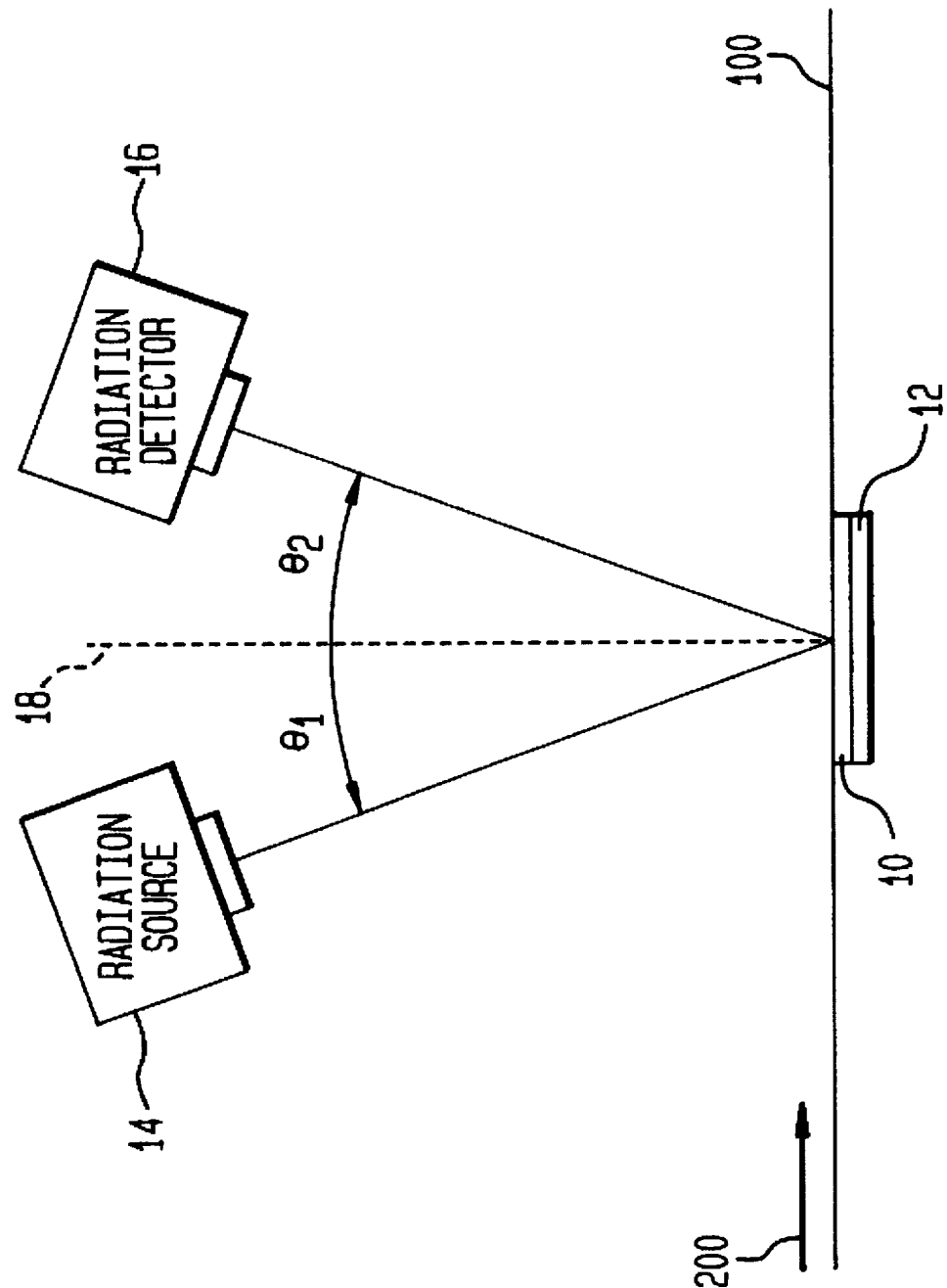

PHOTOELASTIC STRESS SENSOR

STATEMENT OF GOVERNMENT INTEREST

The invention described herein may be manufactured and used by or for the Government of the United States of America for Governmental purposes without the payment of any royalties thereon or therefor.

BACKGROUND OF THE INVENTION

(1) Field of the Invention

The present invention relates generally to stress sensors, and more particularly to a photoelastic stress sensor for detecting shear stress at a material's surface due to a flow thereover.

(2) Description of the Prior Art

Shear stress experienced at a structure's surface due to a flow of fluid or gas can be determined indirectly by measuring the velocity profile next to the surface, and then taking the material derivative. Mathematically, this is expressed by the relationship $$\tau = \mu \frac{du}{dy}\bigg]_{y\to 0} \quad (1)$$

where
- $\tau$ is the shear stress at the surface; $\mu$ is the viscosity of the gas or liquid;
- u is the streamwise velocity; and
- y is the vertical distance from the surface.

While many methods exist to make direct measurements of $\mu$, u, and y, this is not a direct measurement of surface stress $\tau$.

Another indirect method of measuring stress is through hot wire anemometry where a thin wire or film is attached to the surface and heated externally through a control instrument (e.g., a wheatstone bridge). The flow over the surface cools the wire or film and the amount of supply voltage necessary to control a constant temperature is related to the surface shear stress by King's Law.

Methods of direct measurement of surface stress often require a floating element to be provided as part of the surface. A strain gauge is used to measure the movement of the floating element in the presence of flow. The floating element, no matter how small, must maintain a physical and electrical connection to and through the surface in question. Because of the difficulties associated with maintaining such physical and electrical connections, measurements can be contaminated by the connection geometry. Thus, the resulting stress measurement is the drag on the element due to flow plus the non-zero "tear" drag or thrust that occurs due to the connection mechanisms.

Other direct measurement methods require the illumination of active elements located on a surface of the material being examined. However, the use of active element coatings, e.g., liquid crystal coatings, requires that the coating element be electrically energized before measurements can be taken. This requires connections that could contaminate the flow. Furthermore, liquid crystal coatings can be affected by the ambient temperature of the surrounding flow.

SUMMARY OF THE INVENTION

Accordingly, it is an object of the present invention to provide an apparatus for measuring stress at the surface of a material.

Another object of the present invention is to provide an apparatus that directly measures surface stresses caused by a flow of a liquid or gas.

Still another object of the present invention is to provide an apparatus that measures flow-induced surfaces stress without interrupting the flow.

Other objects and advantages of the present invention will become more obvious hereinafter in the specification and drawings.

In accordance with the present invention, a stress detection apparatus has a piece of semiconductor grade, single crystal silicon mounted on the material. The single crystal silicon can be mirror-backed. An infrared source illuminates the single crystal silicon with radiation having a wavelength in the range of 800–1100 nanometers. An infrared detector is focused on the single crystal silicon to monitor the photoelastic effects of illuminating same with the radiation.

BRIEF DESCRIPTION OF THE DRAWING

Other objects, features and advantages of the present invention will become apparent upon reference to the following description of the preferred embodiments and to the drawings, wherein:

The sole figure is a schematic view of the present invention configured for detecting shear stress at the surface of a material as caused by a flow of liquid or gas over the surface of the material.

DESCRIPTION OF THE PREFERRED EMBODIMENT

Referring now to the sole figure, the present invention will be described for the application of detecting and measuring shear stress experienced at the surface of a material due to a flow over such surface. The surface to be examined is referenced by numeral 100 and the flow causing the stress to be detected and measured is referenced by flow arrow 200. As will become apparent from the following description, surface 100 is representative of any surface exposed to a flow such as an air, land or undersea vehicle, or a static structure such as a building, bridge, etc. Flow arrow 200 is representative of any liquid or gaseous flow that may induce stress at surface 100.

In accordance with the present invention, a small piece or wafer 10 of semiconductor grade, single crystal silicon is indented or embedded in surface 100. Typically, wafer 10 is made flush with surface 100 so that it is not directly affected by flow 200 and so that wafer 10 does not disturb flow 200. Wafer 10 is preferably, but not necessarily, backed by mirror 12. A radiation source 14 and radiation detector 16 are positioned remotely from surface 100. Radiation source 14 is any device capable of illuminating wafer 10 with near-infrared radiation in the 800–1100 nanometer wavelength range. Radiation 16 is any device focused on wafer 10 for detecting how the radiation from source 14 interacts with wafer 10 when wafer 10 experiences stress due to flow 200. A variety of such source and detector devices are available from Edmund Scientific Company, Barrington, N.J.

Illumination by source 14 and detection by detector 16 typically occurs in a plane that is normal to wafer 10. As shown, illumination from source 14 can occur along angle $\theta_1$, with respect to dashed line 18 representative of a line normal to wafer 10. Monitoring of wafer 10 would be accomplished by focusing detector 16 from a position on the same or opposite side of line 18 along a direct line of sight at an angle $\theta_2$ where $\theta_1$ and $\theta_2$ can be acute angles equivalent or different in magnitude. Alternatively, both the illumination of wafer 10 and detection of the resulting effects can occur directly above wafer 10 along direct line of sight 18.

The principle of operation of the present invention depends upon the birefringent phenomenon. Many materials are optically sensitive to stress and strain, i.e., they possess the optical properties of polarizing light when under stress and of transmitting light or the principal stress planes with velocities dependent on the stresses. Transmission of stress planes is known as birefringence or double refraction. When wafer 10 is subjected to the specified radiation from source 14, the birefringent effect causes the light to emerge refracted into two orthonormal planes. Because the velocities of light propagation are different in each direction, the light waves experience a phase shift. When the light waves are recombined at detector 16, regions of stress where the wave phases cancel appear black, and regions of stress where the wave phases combine appear light. Therefore, in photoelastic surfaces where complex, fast changing or 3-D stress distributions are present, light and dark fringe patterns (isochromatic fringes) are projected from wafer 10. These fringes are direct manifestations of stress. The use of mirror 12 aids in the direct observation of the fringe patterns from positions normal to wafer 10 or positions angularly displaced from normal line 18 as shown in the figure. A quantitative measure of surface stress can be achieved by calibrating fringe patterns with known levels of stress.

In order to stimulate the above described photoelastic effect, it is necessary to make wafer 10 transparent. The crystal structure of semiconductor grade, single crystal silicon can be made optically transparent by radiation having a wavelength between 800–1100 nanometers.

The advantages of the present invention are numerous. The semiconductor grade, single crystal silicon requires no electrical stimulation. Thus, it is well suited to be embedded in a surface that is to be examined for flow-induced stress since the flow need not be disturbed. The present invention provides for direct measurement of stress with no moving parts. The single crystal silicon is a material that is highly corrosion resistant. In addition, the single crystal silicon can be activated and read from positions that are remote from the surface in question. The single crystal silicon is easily conformed in size and shape to the surface to be examined. The simplicity of the present invention results in an inexpensive approach to detecting and measuring surface stress in a material that can be, but need not be, flow-induced.

The present invention could be adapted for use in the measurement and monitoring of stresses induced in all types of structures. The completely passive nature of the embedded wafer allows for remote monitoring continuously or periodically. An example of this would be the application of the embedded wafer in a bridge structure at a critical stress point. The wafer could be monitored remotely through the optical process described above. The level of induced stress could be obtained by comparison with previous or ground truth measurements. In addition, the present invention would allow a silicon-based sensor to be used in a dual mode. For example, the silicon substrate of a semiconductor pressure transducer could be used to detect stress as described above while the pressure transducer functioned in its normal pressure sensing capacity. This would make it possible to use one sensor to obtain a variety of measurements simultaneously for a structure in question.

It will be understood that many additional changes in the details, materials, steps and arrangement of parts, which have been herein described and illustrated in order to explain the nature of the invention, may be made by those skilled in the art within the principle and scope of the invention as expressed in the appended claims.

What is claimed is:

1. An apparatus for detecting shear stress in a material, comprising:

a piece of single crystal silicon mounted on the material;

a mirror mounted between said piece of single crystal silicon and the material;

an infrared source for illuminating said piece of single crystal silicon with radiation having a wavelength in the range of 800–1100 nanometers; and an infrared detector focused on the illuminated portion of said piece of single crystal silicon for monitoring birefringence induced phase change effects in light emergent therefrom.

2. An apparatus for detecting shear stress at the surface of a material exposed to a flow, comprising:

a mirror-backed single crystal silicon semiconductor wafer embedded in the material such that said wafer is flush with the surface of the material;

an infrared source for illuminating said wafer with radiation to cause said wafer to become birefringent; and an infrared detector focused on the illuminated portion of said wafer for monitoring birefringence induced phase change effects in light emergent therefrom.

3. An apparatus for detecting shear stress in a material comprising:

a piece of single crystal silicon mounted on the material, said piece of single crystal silicon being embedded in the material to be flush with the surface of the material;

an infrared source for illuminating said piece of single crystal silicon with radiation having a wavelength in the range of 800–1100 nanometers; and an infrared detector focused on the illuminated portion of said piece of single crystal silicon for monitoring birefringence induced phase change effects in light emergent therefrom.

4. An Apparatus for detecting shear stress in a material, comprising;

a piece of single crystal silicon mounted on the material;

an infrared source for illuminating said piece of single crystal silicon with radiation having a wavelength in the range of 800–1100 nanometers, said infrared source illuminating said piece of single crystal silicon from a first angle with respect to a line normal to said piece of single crystal silicon; and an infrared detector focused on the illuminated portion of said piece of single crystal silicon for monitoring birefringence induced phase change effects in light emergent therefrom.

5. An apparatus as in claim 4 wherein said infrared detector is focused on said piece of single crystal silicon from a second angle with respect to said line, said first angle and said second angle being equal in magnitude.

6. An apparatus as in claim 5 wherein said infrared source and said infrared detector lie in a plane normal to said piece of single crystal silicon.

7. An apparatus for detecting shear stress at the surface of a material exposed to a flow, comprising:

a mirror-backed single crystal silicon semiconductor wafer embedded in the material such that said wafer is flush with the surface of the material;

an infrared source for illuminating said wafer with radiation having a wavelength in the range of 800–1100 nanometers; and an infrared detector focused on the illuminated portion of said wafer for monitoring birefringence induced phase shift effects in light emergent therefrom.

8. An apparatus as in claim 7 wherein said infrared source and said infrared detector lie in a plane normal to said wafer such that said radiation and said effects of illuminating reside substantially in said plane.

9. An apparatus as in claim 8 wherein said infrared source and said infrared detector are disposed on opposing sides of a line normal to said wafer.

10. Apparatus as in claim 2 wherein said infrared detector is focused on said portion of said wafer along a direct line of sight.

11. An apparatus as in claim 2 wherein said infrared source and said infrared detector lie in a plane normal to said wafer.

12. An apparatus as in claim 11 wherein said infrared source and said infrared detector are disposed on opposing sides of a line normal to said wafer.

13. An apparatus for detecting shear stress in a material, comprising;
   a piece of single crystal silicon mounted on the material;
   an infrared source for illuminating said piece of single crystal silicon with radiation having a wavelength in the range of 800–1100 nanometers; and
   an infrared detector focused on the illuminated portion of said piece of single crystal silicon for monitoring birefringe induced phase change effects in light emergent therefrom, wherein said infrared detector is focused on said portion of the single crystal silicon along a direct line of sight.

14. Apparatus as in claims 13 wherein said phase change effects are manifested in the form of responses of the infrared detector to light and dark fringe patterns produce by projection of birefringence from the single crystal silicon.

15. Apparatus as in claim 7 wherein said infrared detector is focused on said portion of said wafer along a direct line of sight.

16. Apparatus as in claim 15 wherein said phase change effects are manifested in the form of responses of the infrared detector to light and dark fringe patterns produce by projection of birefringence from the wafer.

17. Apparatus as in claim 10 wherein said phase change effects are manifested in the form of responses of the infrared detector to light and dark fringe patterns produce by projection of birefringence from the wafer.

\* \* \* \* \*